United States Patent
Ishida et al.

(10) Patent No.: US 7,749,791 B2
(45) Date of Patent: Jul. 6, 2010

(54) SENSOR AND METHOD OF MANUFACTURING THE SAME

(75) Inventors: Yohei Ishida, Kawasaki (JP); Hirokatsu Miyata, Hadano (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/608,979

(22) Filed: Oct. 29, 2009

(65) Prior Publication Data
US 2010/0047948 A1 Feb. 25, 2010

Related U.S. Application Data

(62) Division of application No. 11/270,568, filed on Nov. 10, 2005.

(30) Foreign Application Priority Data

| Nov. 12, 2004 | (JP) | 2004-329046 |
| Dec. 27, 2004 | (JP) | 2004-376368 |
| Jun. 7, 2005 | (JP) | 2005-167114 |

(51) Int. Cl.
*H01L 21/02* (2006.01)
(52) U.S. Cl. ............... 438/49; 257/E21.002
(58) Field of Classification Search ............. 438/48, 438/49, 51, 54; 428/312.2, 312.8; 257/E29.31
See application file for complete search history.

(56) References Cited

U.S. PATENT DOCUMENTS

| 4,774,129 | A | 9/1988 | Komiyama et al. |
| 6,120,891 | A | 9/2000 | Balkus, Jr. et al. |
| 2002/0127386 | A1 | 9/2002 | Ogawa et al. |
| 2003/0175569 | A1 | 9/2003 | Inagaki et al. |
| 2006/0273312 | A1 | 12/2006 | Miyata et al. |
| 2007/0023289 | A1 | 2/2007 | Miyata et al. |

FOREIGN PATENT DOCUMENTS

| JP | 4-79540 | 12/1992 |
| JP | 7-128268 | 5/1995 |
| JP | 2002-308623 | 10/2002 |

OTHER PUBLICATIONS

Arijit Chowdhuri, et al., "Response speed of SnO2-based H2S gas sensors with CuO nanoparticles", Applied Physics Letters, vol. 84, No. 7, Feb. 16, 2004, pp. 1180-1182.
Kenji Wada, et al., "Hydrogen sensing properties of SnO2 subjected to surface chemical modification with ethoxysilanes", Sensors and Actuators B 62, 2000, pp. 211-219.

*Primary Examiner*—Roy K Potter
(74) *Attorney, Agent, or Firm*—Fitzpatrick, Cella, Harper & Scinto

(57) ABSTRACT

A sensor comprising a semiconductor film having a plurality of mesopores and containing an oxide, and electrodes electrically connected to the semiconductor film, wherein at least part of surfaces in the mesopores is coated with an organic material.

7 Claims, 9 Drawing Sheets

US 7,749,791 B2

SENSOR AND METHOD OF MANUFACTURING THE SAME

This application is a divisional of application Ser. No. 11/270,568, filed Nov. 10, 2005, the contents of which are incorporated herein by reference.

BACKGROUND OF THE INVENTION

1. Field of the Invention

The present invention relates to a sensor for detecting a substance that is adsorbed to and/or desorbed from the surface of semiconductor and a method of manufacturing the same. This invention can be applied to a gas sensor and a bio sensor.

2. Related Background Art

Gas sensors and bio sensors of various types have been proposed to detect the presence or absence of a substance and its concentration.

Among such sensors, semiconductor type sensors are adapted to detect a substance, utilizing a metal oxide semiconductor having a property of changing its resistance in response to adsorption or desorption of the substance. Thus, semiconductor type sensors find applications in gas escape alarms and so on. Oxide semiconductors, tin oxide in particular are popularly used for gas sensors. One of the challenges to existing gas sensor elements is selective detection of a gas as an object of detection.

Due to absorption and/or desorption of molecules that are adsorbed to the surface of a metal oxide semiconductor, the width of the depletion layer that is present on the surface of the metal oxide changes as a function of the adsorption or desorption. Thus, metal oxide semiconductor elements that are used in gas sensor elements are mostly devised to detect the change in the electric resistance of the semiconductor element. In the case of tin oxide, for instance, oxygen molecules adsorbed to the surface of tin oxide are removed as a result of a chemical reaction (combustion) of a gas and the oxygen adsorbed to the surface of tin oxide, and consequently the width of the depletion layer is reduced to by turn lower the electric resistance of the tin oxide.

Due to the above-described principle of operation, it is difficult to detect only a target gas in an atmosphere where gases of a plurality of different types that can change the width of the depletion layer coexist when a single metal oxide semiconductor is used.

Therefore, it is an object of the present invention to provide a sensor that can detect only a target gas to be detected.

SUMMARY OF THE INVENTION

In an aspect at the present invention, the above object is achieved by providing a sensor comprising: a semiconductor film having a plurality of mesopores and containing an oxide; and electrodes electrically connected to the semiconductor film; at least part of surfaces in the mesopores being coated with an organic material.

In another aspect of the present invention, there is provided a sensor comprising: a semiconductor film having a plurality of mesopores and containing an oxide; and electrodes electrically connected to the semiconductor film; at least part of surfaces in the mesopores being coated with an oxide different from said oxide.

In still another aspect of the present invention, there is provided a sensor comprising: a semiconductor film having a plurality of mesopores and containing a tin oxide; and electrodes electrically connected to the semiconductor film; particles of an inorganic material being held in the mesopores.

In still another aspect of the present invention, there is provided a method of manufacturing a sensor comprising: preparing a reaction solution containing a metal compound and a surfactant and applying the reaction solution onto a substrate; holding the substrate with the reaction solution applied thereto in a steam-containing atmosphere and forming a film containing a metal oxide and the surfactant on the substrate; removing the surfactant from the film and producing a film having a plurality of mesopores; and causing the mesopores to hold particles of an inorganic material.

In still another aspect of the present invention, there is provided a method of manufacturing a sensor comprising: preparing a reaction solution containing a metal compound and a surfactant and applying the reaction solution onto a substrate; holding the substrate with the reaction solution applied thereto in a steam-containing atmosphere and forming a film containing a metal oxide and the surfactant on the substrate; removing the surfactant from the film and producing a film having a plurality of mesopores; and coating at least part of surfaces in the mesopores with an organic material.

In still another aspect of the present invention, there is provided a method of manufacturing a sensor comprising: preparing a reaction solution containing a metal compound and a surfactant and applying the reaction solution onto a substrate; holding the substrate with the reaction solution applied thereto in a steam-containing atmosphere and forming a film containing a metal oxide and the surfactant on the substrate; removing the surfactant from the film and producing a film having a plurality of mesopores; and coating at least part of surfaces in the mesopores with an inorganic oxide.

Thus, the present invention can provide a sensor that can selectively detect molecules of a specific gas.

DETAILED DESCRIPTION OF THE PREFERRED EMBODIMENTS

Now, the present invention will be described in detail. Firstly, the present invention will by summarily described by referring to FIGS. 1, 2, 3, 4 and 5.

Figure 1:
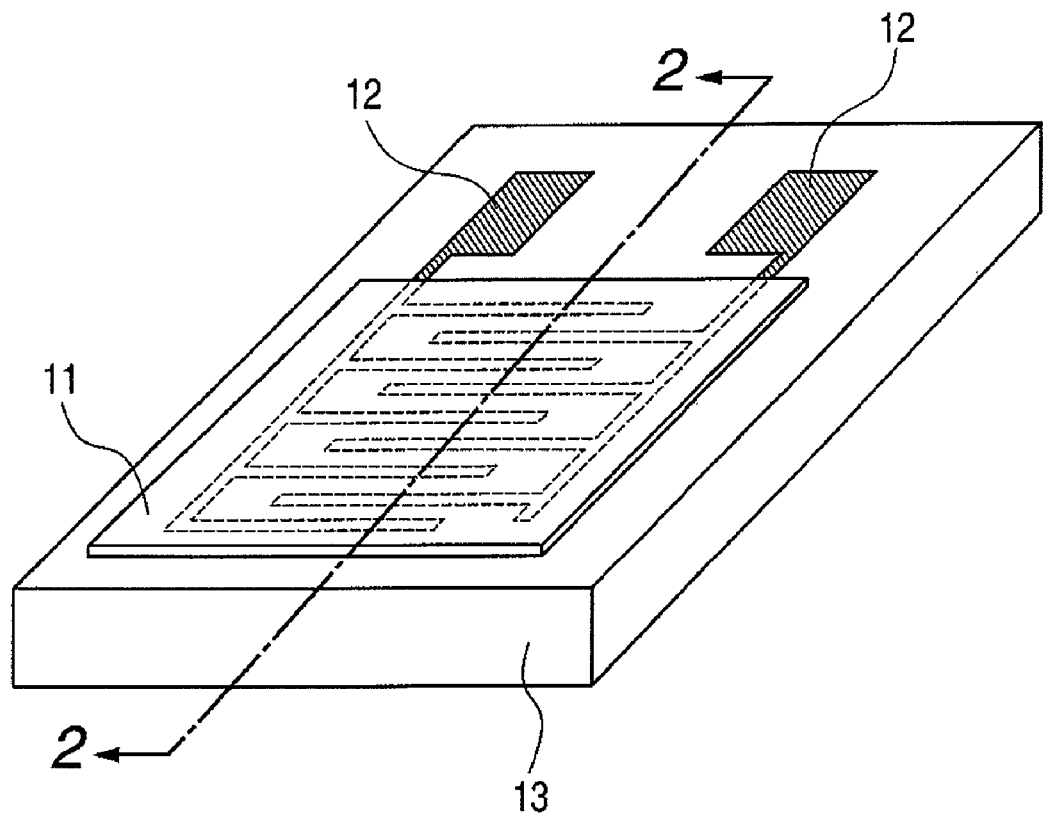
FIG. 1 is a schematic perspective view of a sensor according to the invention, showing its configuration.
Figure 2:
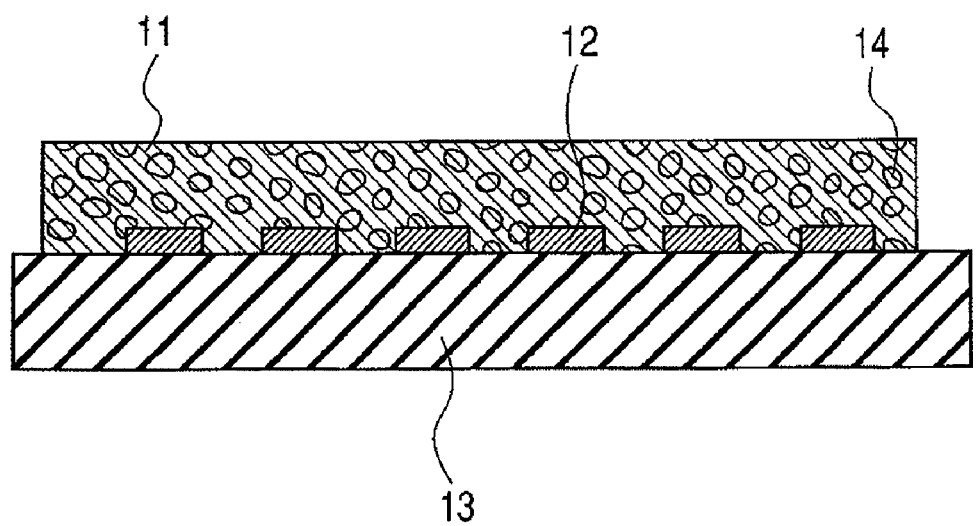
FIG. 2 is a schematic cross sectional view of the sensor of FIG. 1.
Figure 3:
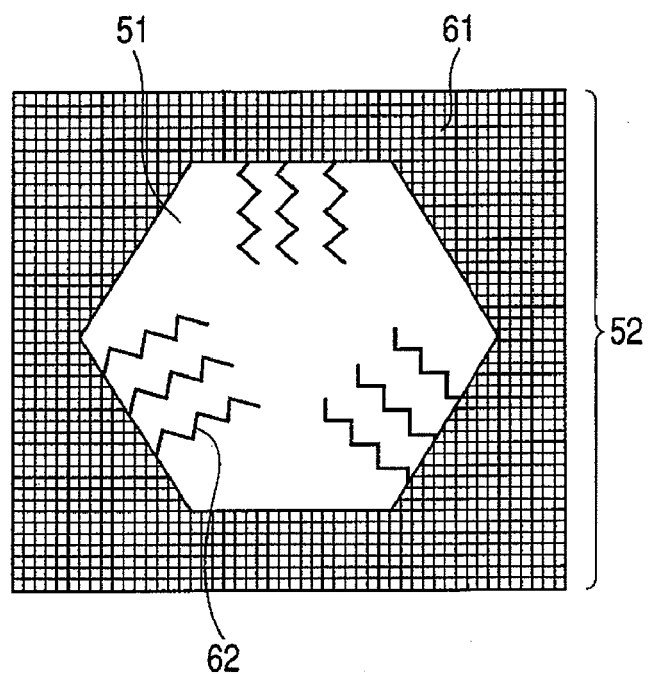
FIG. 3 is an enlarged schematic view of a mesopore in FIG. 2.
Figure 4:
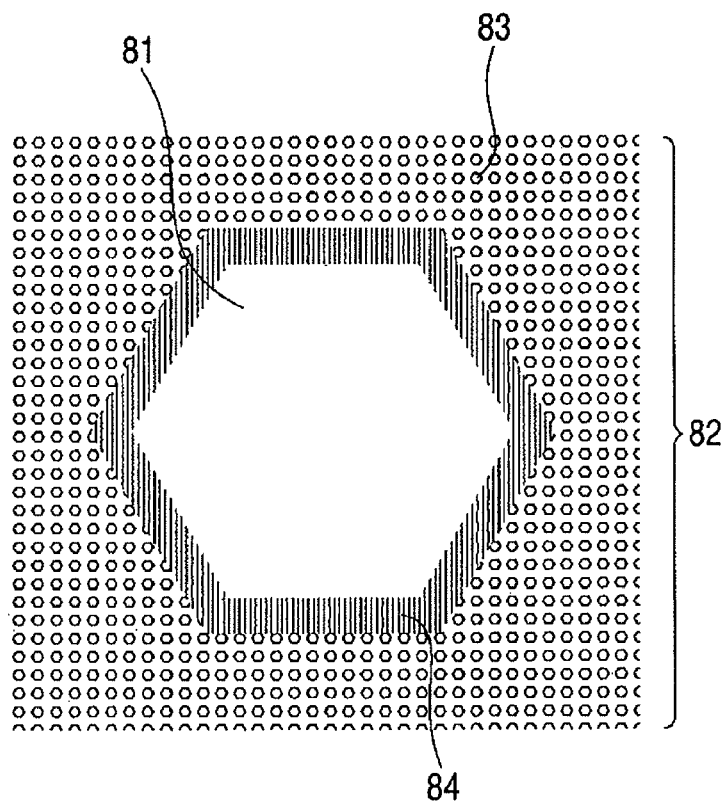
FIG. 4 is an enlarged schematic view of a mesopore in FIG. 2.
Figure 5:
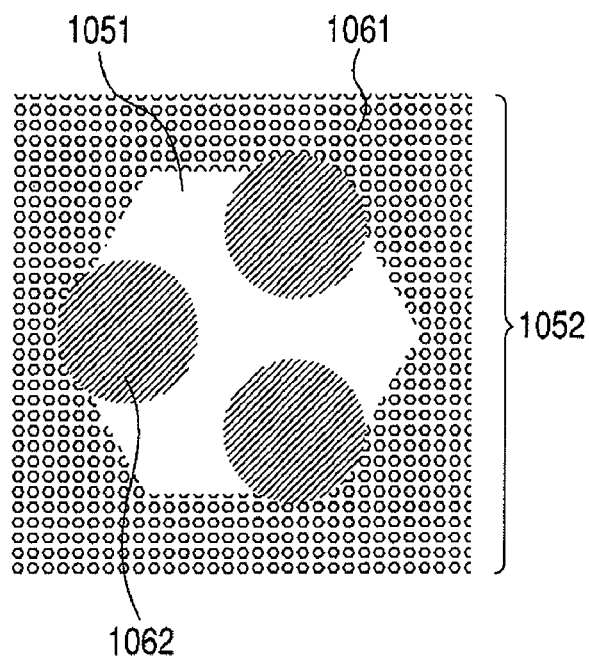
FIG. 5 is an enlarged schematic view of a mesopore in FIG. 2.

FIG. 1 is a schematic perspective view of a sensor according to the invention, showing its configuration. A pair of electrodes 12, 12 is arranged on a substrate 13 and a porous oxide semiconductor film 11 is formed thereon as a sensing section. FIG. 2 is a schematic cross sectional view of the sensor of FIG. 1 taken along line 2-2. A pair of electrodes 12, 12 and a porous oxide semiconductor film 11 are formed on the substrate 13. The porous oxide semiconductor film 11 has a plurality of mesopores 14. While mesopores will be described in detail hereinafter, FIGS. 3, 4 and 5 provide enlarged views of mesopores. FIG. 3 is an enlarged schematic view of a mesopore, showing that the surface in the mesopore is coated with an organic material. FIG. 4 is another enlarged schematic view of a mesopore, showing that the surface in the mesopore is coated with an oxide different from the oxide contained in the porous oxide semiconductor film 11. FIG. 5 is still another enlarged schematic view of a mesopore, showing that particles of an inorganic material are held in the mesopore. A sensor according to the present invention is so devised as to be capable of selectively detecting gas molecules by coating the surfaces in the mesopores or causing the surfaces in the mesopores to hold particles of an inorganic material.

A "mesopore" is defined to be a pore with a pore size between 2 nm and 50 nm according to the classification of IUPAC. A pore with a pore size less than 2 nm is defined to be a micropore, while a pore with a pore size greater than 50 nm is defined to be a macropore.

The specific surface area is smaller in a structure having macropores whose sizes are larger than those of mesopores than in a structure having a plurality of mesopores. A structure having a smaller specific surface area can hold a lesser amount of particles of an inorganic material or a lesser amount of an oxide of an organic material in the pores. Additionally, such a structure can adsorb a lesser amount of gas molecules to be detected. On the other hand, in a structure having micropores whose sizes are smaller than those of mesopores, it can be difficult to introduce particles of an inorganic material into the micropores and quickly adsorb gas molecules to or desorb gas molecules from the surfaces of the micropores.

Therefore, a structure having mesopores can most suitably be used for a gas sensor or a bio sensor to detect small molecules.

A "porous oxide semiconductor film" is preferably a continuous film. Such a film can show a higher efficiency of utilization and a higher response speed than a porous oxide semiconductor film 11 that is formed as an aggregate of particles when used for a sensor. When the porous oxide semiconductor film 11 is an aggregate of particles in a structure, the structure shows a smaller specific surface area than a structure having mesopores. Then, the efficiency of utilization of the element may not become high and the response speed may be low when it is used for a sensor.

The "oxide contained in the porous oxide semiconductor film" is preferably a metal oxide that shows characteristics of semiconductor. Examples of metal oxides that show such characteristics include tin oxide ($SnO_2$), zinc oxide (ZnO), niobium oxide ($Nb_2O_5$) and tungsten oxide ($WO_3$), of which tin oxide ($SnO_2$) can preferably be used for the purpose of the present invention.

Any "organic material" that can selectively catch the detection substance, or the detection substances, and change the electric resistance of the metal oxide may be used. Particularly, organic materials containing one or more than one Lewis bases are preferable candidates. Such organic materials have any of the functional groups and bonds listed below as examples.

Examples of functional groups include halogens, alcohols, amines, nitrites, nitros, sulfides, sulfoxides, sulfones, thiols, carbonyls, aldehydes, ketones, carbonic acids, amides, carbonic acid chlorides, carbonic acid anhydride and organic carbonic acids.

Examples of bonds include ether bonds, ester bonds and amide bonds.

For the purpose of the present invention, the "oxide different from the oxide contained in the porous oxide semiconductor film 11" may be any oxide that can selectively separate a specific gas or reacts with a specific gas and can change the electric resistance of the porous oxide semiconductor film. Examples of such oxides include silicon oxide. Silicon oxide selectively allows a gas having a small molecular weight to pass through it. More specifically, silicon oxide selectively allows hydrogen to pass through it so that it can be used for a hydrogen sensor.

"Particles of an inorganic material" may be those of any material that can separate or decompose the detection substance from gas or liquid containing the detection substance by means of a catalytic effect. Examples of inorganic materials that can be used for the purpose of the present invention include palladium (Pd), platinum (Pt), ruthenium (Ru), silver (Ag), cobalt (Co), gold (Au), nickel (Ni), copper (Cu), manganese (Mn), iron (Fe), chromium (Cr) and vanadium (V). Particularly, from the viewpoint of hydrogen gas, palladium (Pd) and platinum (Pt) are preferable because they show an excellent selectivity relative to hydrogen gas.

Particles of any metal oxide having a similar effect may also be used. Examples of such metal oxides include copper oxide (II) (CuO), nickel oxide (NiO) and cobalt oxide (CoO), of which copper oxide (II) (CuO) may preferably be used for a sensor for detecting hydrogen sulfide because it is highly selective relative to hydrogen sulfide.

Figure 6A:
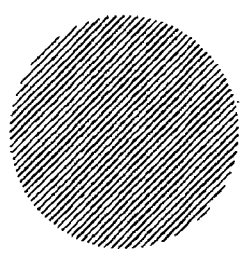
FIGS. 6A, 6B, 6C and 6D are schematic illustrations of particles of an inorganic material.
Figure 6B:
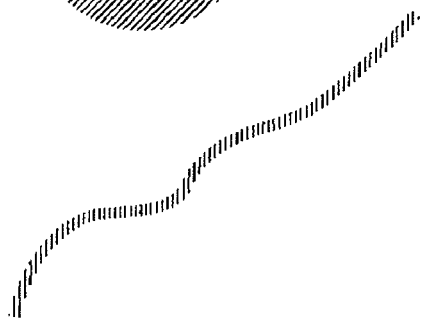
Figure 6C:
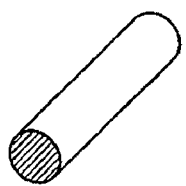
Figure 6D:
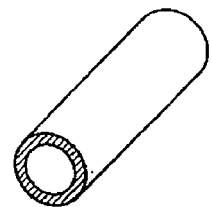

Particles of an inorganic material may show any profile so long as they can be introduced into pores. For examples, they may show any of the profiles illustrated in FIGS. 6A, 6B, 6C and 6D that include spherical (FIG. 6A), wire-shaped (FIG. 6B), rod-shaped (FIG. 6C) and tubular (FIG. D).

Particles of an inorganic material may have any size so long as they can be held in pores to prevent gas from diffusing into the pores. If particles of an inorganic material are spherical, it is preferable that their sizes are smaller than the sizes of the pores.

Figure 7:
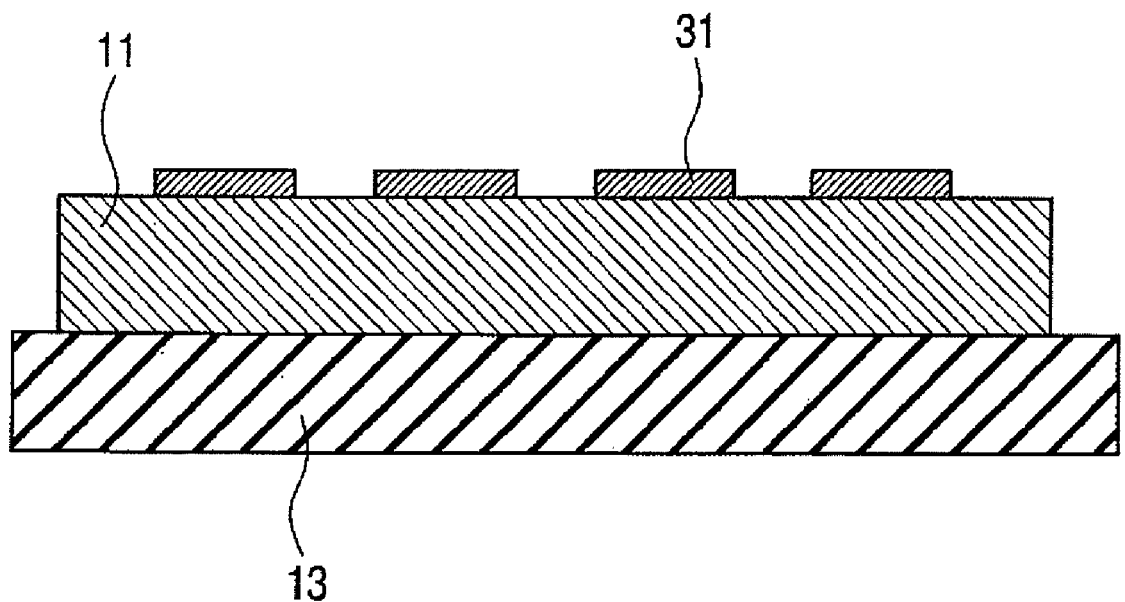
FIG. 7 is a schematic cross sectional view of an embodiment of sensor according to the invention.
Figure 8:
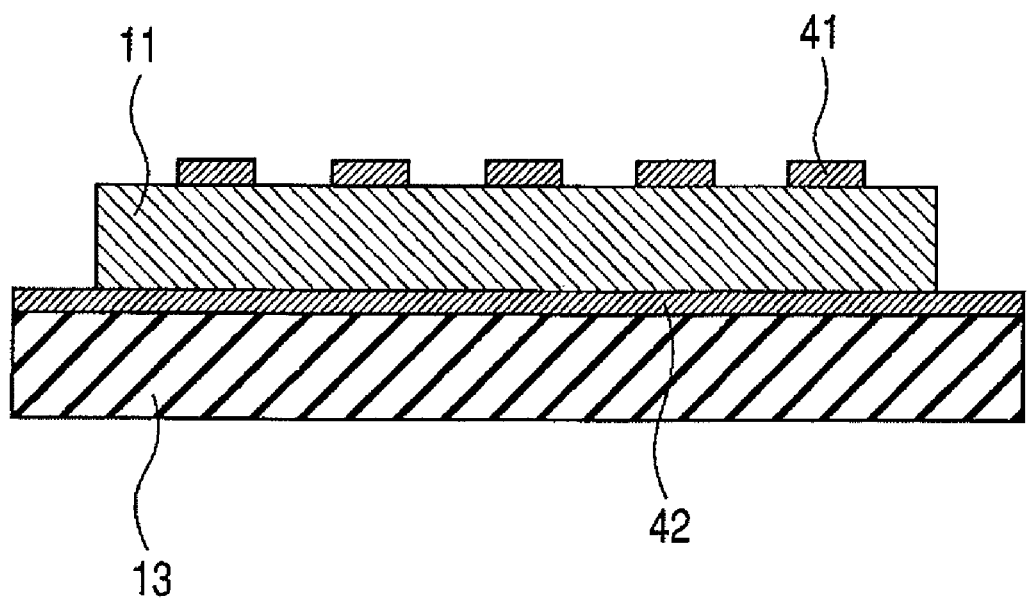
FIG. 8 is a schematic cross sectional view of another embodiment of sensor according to the invention.

"Electrodes" may be comb-like electrodes as shown in FIG. 1 that may be realized by bonding a plurality of electrodes. For example, an arrangement where a plurality of electrodes are formed on the porous oxide semiconductor film as shown in FIG. 7 or an arrangement where electrodes are formed on and under the porous oxide semiconductor film as shown in FIG. 8 may be used for the purpose of the present invention. The electrodes are connected to an electric circuit to measure the change in the electric resistance of the porous material and determine if there is the detection substance, or the target substance to be detected.

For the purpose of improving the sensitivity of a sensor, a heater and/or microcrystals may be used and the arrangement and the pore sizes of mesopores (fine pores) may be defined in a manner as described below.

1. Heater

A heater may be arranged in order to accelerate the adsorption/desorption reaction of the detection substance and heat the substrate and the porous oxide semiconductor film. On a cold site, it is convenient to set the temperature of the sensor optimally for the reaction with gas. A heater is preferably arranged at a position where it is held in contact with the porous oxide semiconductor film, although some other layer may be disposed between the porous oxide semiconductor film and the heater.

2. Arrangement and Pore Size of Mesopores

Figure 9:
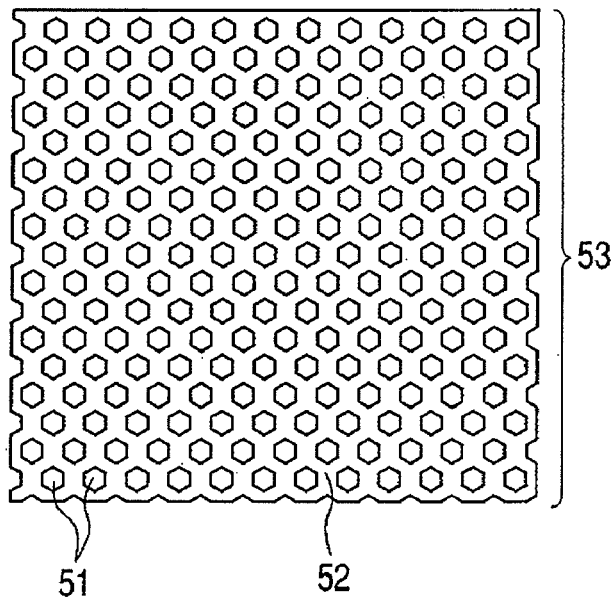
FIG. 9 is a schematic illustration of an arrangement of mesopores.

FIG. 9 shows mesopores that are arranged to show a two-dimensional hexagonal structure. However, the arrangement of fine pores is not limited to such a structure. For example, they may alternatively be arranged to show a distorted two-dimensional hexagonal structure, a cubic structure or a three-dimensional hexagonal structure. The fine pores may have a unique size or different sizes that do not show any clear periodicity.

The porous oxide semiconductor film 11 preferably shows one or more than one diffraction peaks in the angular region that corresponds to the structural periodicity of not less than 1 nm in X-ray diffraction analysis. This is because the pore arrays in the porous oxide semiconductor film shows a regular structural periodicity, mesopores are densely arranged to raise the specific surface area thereof in the porous oxide semiconductor film.

A technique for measuring adsorption isotherms of gas such as nitrogen gas is generally used to evaluate the distribution of fine pores in a porous oxide semiconductor film 11 and the distribution of fine pores are computationally determined from the obtained adsorption isotherms typically by means of the Berret-Joyner-Halenda (BJH) analysis method.

Thus, the distribution of fine pores of a porous oxide semiconductor film 11 to be used for the purpose of the invention are determined by the BJH method from the data obtained by observing the nitrogen gas adsorption of the fine pores. It is preferable that the distribution of fine pore diameters shows a unique maximum value and not less than 60% of the diameters of the fine pores are found within a range not greater than 12 nm.

3. Microcrystals

For the purpose of the present invention, the pore walls of the porous oxide semiconductor film 11 preferably contain microcrystals. When, for example, tin oxide is used, it was found as a result of a series of intensive researches conducted by the inventors of the present invention on the correlation between the particle diameters of tin oxide and the sensitivity of detecting the detection substance that an enhanced level of sensitivity can be achieved when the diameters of microparticles are not greater than 10 nm, particularly when the diameters are not greater than 6 nm.

The diameters of microcrystals can be controlled by controlling the conditions of the processing step using steam and the step of removing the surfactant, which will be described in greater detail hereinafter.

(Method of Manufacturing Sensor)

Now, a method of manufacturing a sensor will be described below.

Figure 10:
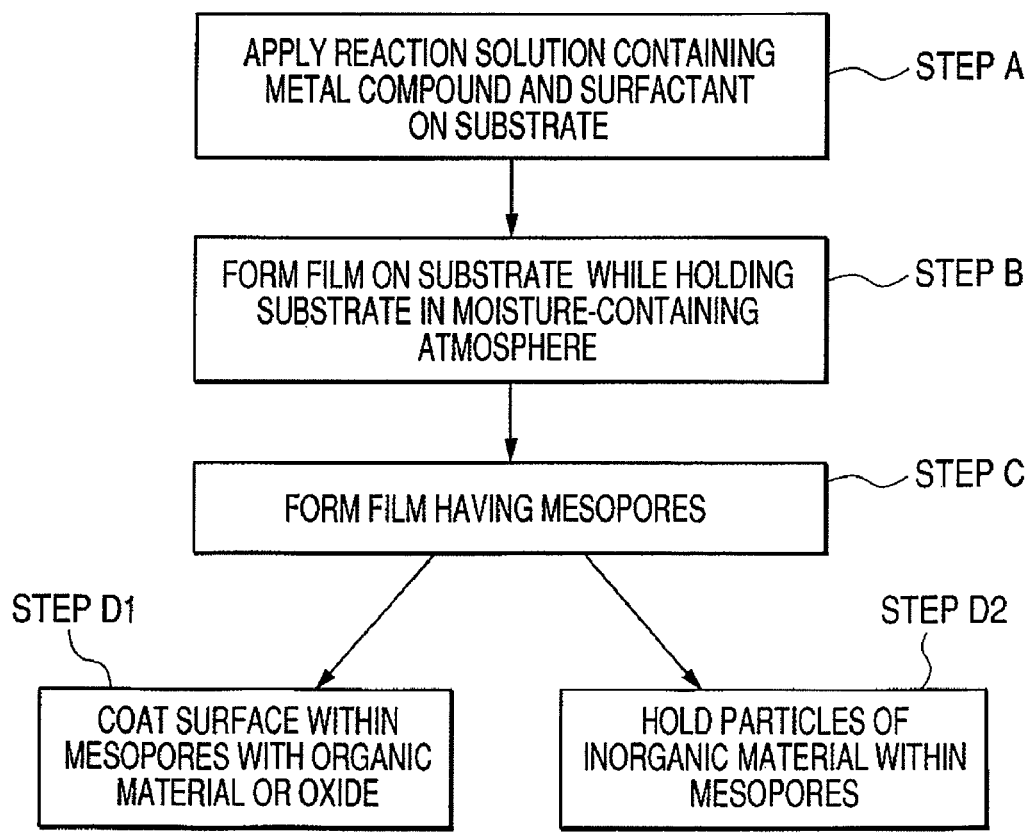
FIG. 10 is a flowchart of a method of manufacturing a sensor according to the invention.

FIG. 10 is a flowchart of a method of manufacturing a porous oxide semiconductor film for the purpose of the present invention.

Referring to FIG. 10, Step A is a step of preparing a reaction solution containing a metal compound and a surfactant and applying the reaction solution onto a substrate. Step B is a step of holding the substrate, to which the reaction solution has been applied, in a steam-containing atmosphere and forming a film containing the metal oxide and the surfactant. Step C is a step of removing the surfactant from the film and forming a plurality of mesopores. Step D1 is a step of coating at least part of surfaces in the mesopores with an organic material or an oxide. Step D2 is a step of holding particles of an inorganic material in the mesopores.

As a result of carrying out Steps A and B, a filmy precursor of a porous oxide semiconductor film that is made of an aggregate of the surfactant and has a region that subsequently makes mesopores is formed on the substrate.

Such a structure is prepared by the process that the surfactant produces a micelle on the substrate to operate as a mold for producing mesopores (fine pores) and the metal compound forms the walls of the fine pores.

As the precursor of the porous oxide semiconductor film is held in a steam-containing atmosphere in Step B, the regularity of the fine pore structure of the precursor of the porous oxide semiconductor film is improved and, at the same time, the oxide semiconductor that is amorphous immediately after the application of the reaction solution is induced to become crystallized by steam.

Then, the surfactant is removed and a porous oxide semiconductor film is produced as a result of carrying out the Step C. Subsequently, the sensor becomes provided with the function of selectively detecting the detection substance as a result of modifying the film surface and the pore surfaces of the porous oxide semiconductor film and holding particles of the inorganic material in the pores as a result of carrying out Steps D1 and D2.

Thereafter, electrodes may be formed on the porous oxide semiconductor film for the purpose of detecting the change in the electric resistance of the porous oxide semiconductor film. The electrodes may be formed in any of the above-described steps, after Steps D1 and D2 or before Step A so long as the electrodes can be connected to the porous oxide semiconductor film.

Now, each of the above listed steps will be described in greater detail below.

(Step A: Step of Preparing a Reaction Solution Containing a Metal Compound and a Surfactant and Applying the Reaction Solution onto a Substrate)

In Step A, firstly a reaction solution containing a metal compound and a surfactant is prepared.

(A-1: Preparation of a Reaction Solution)

The metal compound is a material for preparing an oxide semiconductor and contains, for example, tin (Sn), zinc (Zn), tungsten (W) or niobium (Nb). Particularly, a metal compound containing tin is preferably used.

Now, the preparation of reaction solution will be described in terms of a tin compound.

Tin compounds that can be used for the purpose of the present invention include chlorides such as tin chloride (I) ($SnCl_2$) and tin chloride (II) ($SnCl_4$) and tin alkoxides such as tin isopropoxide and tin ethoxide, although tin compounds that can be used for the purpose of the present invention are not limited to those listed above.

The surfactant produces a micelle that operates as a mold for producing fine pores.

A non-ionic surfactant is preferably used for the surfactant.

Non-ionic surfactants containing ethylene oxide are particularly preferable. Examples of such surfactants include the following:

tri-block-copolymers such as <$HO(CH_2CH_2O)_{20}(CH_2CH(CH_3)O)_{70}(CH_2CH_2O)_{20}H$> polyoxyethylene (10) dodecylether <$C_{12}H_{25}(CH_2CH_2O)_{20}H$> polyoxyethylene (10) tetradecylether <$C_{14}H_{29}(CH_2CH_2O)_{10}OH$> polyoxyethylene (10) hexadecylether <$C_{16}H_{33}(CH_2CH_2O)_{10}OH$> polyoxyethylene (10) stearylether <$C_{18}H_{37}(CH_2CH_2O)_{10}OH$>.

Of the above-listed surfactants, triblock copolymers are preferably used.

While alcohols such as methanol and ethanol are preferable candidate of solvent, a mixed solvent of alcohol and water can also be used. In short, any solvent that is liquid and can dissolve the metal compound and the surfactant may be used for the purpose of the present invention. Acid or the like may be appropriately added to the solvent as catalyst.

Thus, the reaction solution is prepared in a manner as described above.

(A-2 Application of the Reaction Solution)

The prepared reaction solution is then applied onto a substrate.

A substrate that is chemically stable relative to the reaction solution and hence hardly chemically reacts with the reaction solution is preferably used. Examples of such substrates include glass substrates, ceramic substrates, resin substrates and metal substrates. Of course, flexible film such as plastic film may also be used for the substrate.

The electrodes and the porous material can be connected with ease after Steps B and C, which will be described hereinafter, by using a substrate on which electrodes are formed as shown in FIGS. 1 and 2.

Examples of effective techniques that can be used for applying the reaction solution onto the substrate easily in a short period of time include the casting, dip coating and spin coating.

Techniques other than those listed above such as spray coating, which is highly suitable for mass production, may also be used so long as such techniques can be used to effectively apply the reaction solution onto the substrate.

Thus, the reaction solution is applied onto the substrate in the above-described manner. Note, however, that it is preferable to dry the reaction solution (particularly solvent) on the substrate after Step A and before Step B.

For example, after Step A, it is preferable to carry out a drying step of drying the solvent in a temperature range between 25 and 50° C. and a humidity range between 10 and 30% before moving to Step B.

As a result of such an additional step, the uniformity of the film will be improved.

(Step B: Holding the Substrate, to which the Reaction Solution has been Applied, in a Steam-Containing Atmosphere and Forming a Film Containing the Metal Oxide and the Surfactant on the Substrate)

Then, the substrate which the reaction solution has been applied to and dried is held in a steam-containing atmosphere and a precursor of a porous oxide semiconductor film is formed.

The relative humidity of the steam-containing atmosphere of Step B is preferably not lower than 40% and not higher than 100% and the temperature of the steam-containing atmosphere is preferably not higher than 100° C.

However, conditions out of the above-defined ranges may be used so long as it is possible to form the target substance, which is a precursor of a porous oxide semiconductor film.

As a result of carrying out this step, the continuity of the film is remarkably improved and, at the same timer the uniformity of mesopores in the porous oxide semiconductor and hence the structural regularity of the porous oxide semiconductor are also improved.

During Step B of holding the substrate, to which the reaction solution is applied in a steam-containing atmosphere, the crystallization of the oxide semiconductor progresses.

The duration of the above process using steam may be appropriately determined according to the level of crystallinity to be achieved.

(Step C: Removing the Surfactant from the Film and Forming a Plurality of Mesopores)

While a number of techniques may be available for removing the surfactant, a baking process of applying heat to the surfactant to decompose and remove it is preferable because it is simple and provides an advantage of accelerating the crystallization of the oxide semiconductor present on the fine pore walls.

However, it should be noted that, when the baking temperature is high, the crystallization of the oxide semiconductor progresses quickly but the pore structure may tend to become irregular.

Therefore, when removing the surfactant by means of a baking process, it is necessary to select an optimum baking temperature level so that the regularity of the pore structure may be maintained.

When the material of the substrate can be deformed in high temperatures probably because the substrate is made of a plastic material and hence it is difficult to conduct a baking process, a technique of extracting the surfactant by means of a supercritical fluid or a solvent may feasibly be used.

When the surfactant is extracted by means of a supercritical fluid or a solvent, it is possible to hold the density of hydroxyl groups on the pore surfaces to a high level after removing the surfactant. As a result, it is possible to improve the density of the modification using the organic material.

The surfactant can be decomposed and removed by means of other techniques such as irradiation of UV rays and oxidation/decomposition by ozone. For the purpose of the present invention, techniques that can be used for decomposing and removing the surfactant are not limited to the above listed ones and any appropriate method may be used so long as it can maintain the pore structure of the porous oxide semiconductor film.

(Step D1: Coating at Least Part of Surfaces in the Mesopores with an Organic Material or an Oxide)

In this step, the surfaces of the pores and the film surface of the porous oxide semiconductor film are modified by means of a substance different from that of the porous oxide semiconductor film.

Substances that can be used for modifying the surfaces of the fine pores include organic materials and inorganic materials.

Thus, organic materials and inorganic materials will be described separately.

1. When the Substance for Modifying the Pore Surfaces is an Organic Material

While any appropriate method may be used to securely bond an organic material to the surface of the porous oxide semiconductor film 11 by means of covalent bonds, a method of producing covalent bonds by means of a silane coupling agent may preferably be used for the purpose of the present invention. This is because the organic material can be bonded to the surface of an oxide semiconductor with ease when a silane coupling agent is used. After depositing the organic material on the surfaces of the pores of the porous oxide semiconductor film 11 by means of a silane coupling agent, the functional groups of the organic material may be modified and/or replaced by other functional groups by way of a chemical reaction.

2. When the Substance for Modifying the Pore Surfaces is Silicone Oxide

While any appropriate method may be used to modify the surfaces of the fine pores by means of silicon oxide so long as the deposited silicon oxide does not clog the fine pores, it is preferable to bond a silicon compound to the surfaces of the fine pores by means of a silane coupling agent and subsequently transform the silicon compound into silicon oxide by means of a heat treatment in an oxidizing atmosphere.

As a result of the above-described step, the surfaces of the fine pores can be coated relatively uniformly with silicon oxide.

(Step D2: Holding Particles of an Inorganic Material in the Mesopores)

In this step, particles of an inorganic material are held in the inside of the pores of the porous oxide semiconductor film.

Any appropriate method may be used for introducing particles of such a material into the inside of the pores so long as they do not significantly change the pore structure of the porous oxide semiconductor film and remarkably reduce their specific surface areas.

When metal particles are to be held in the pores of the porous oxide semiconductor film, it is preferable to introduce a metal compound that is dissolved in a solution such as aqueous solution into the pores of the porous oxide semiconductor film and produce particles of metal in the pores by reducing the metal compounds.

If, for example, palladium is introduced, a solution containing a palladium compound is firstly introduced into the pores of the porous oxide semiconductor film and the palladium compound is subsequently subjected to a reduction process to produce palladium particles in the pores.

Examples of palladium compounds that can be used for the purpose of the invention include palladium acetate (Pd($CH_3COO)_2$), palladium chloride (II) ($PdCl_2$), palladium nitrate (II) (Pd($NO_3)_2$), dinitroamine palladium (II) ([Pd($NO_2)_2(NH_3)_2$]), dichlorodiamine palladium (II) ([Pd($NH_3)_2$$Cl_2$]), tetraamine palladium (II) dichloride ([Pd($NH_3)_4$]$Cl_2.nH_2O$) and tetraamine palladium (II) nitrate (Pd($NH_3)_4$($NO_3)_2$), any of which may be used so long as it can produce palladium particles in the pores by way of the above-described process.

If, for example, platinum is introduced, a solution containing a platinum compound is firstly introduced into the pores of the porous oxide semiconductor film and the platinum compound is subsequently subjected to a reduction process to produce platinum particles in the pores.

Examples of platinum compounds include chloroplatinic (IV) acid ($H_2[PtCl_6].6H_2O$), dinitrodiamineplatinum (II) ([Pt($NO_2)_2(NH_3)_2$]), tetraaminedichloroplatinum (II) ([Pt($NH_3)_4$]$Cl_2.H_2O$), potassium hexahydroxoplatinate (IV) ($K_2$[Pt($OH)_6$]) and platinum nitrate (IV) (Pt($NO_3)_4$), any of which may be used so long as it can produce platinum particles in the pores by way of the above-described process.

When particles of an oxide are to be held in the pores of the porous oxide semiconductor film, it is preferable to firstly form metal particles, subsequently introduce the metal particles into the pores of the porous oxide semiconductor film and then oxidize the metal particles in the pores to produce oxide particles.

For example, if particles of copper oxide are to be held in the pores, copper (Cu) particles are formed first and then the porous oxide semiconductor film is immersed into a solution containing copper particles in a dispersed state. Subsequently, the copper particles are subjected to an oxidation process to produce copper (II) oxide (CuO) in the pores.

As described above, it is possible to form a porous oxide semiconductor film that is provided with mesopores having a uniform pore size and microcrystal arranged in the pore walls and holding particles of an inorganic material in the pores as a result of carrying out Steps A through E.

Besides, it is possible to form a porous oxide semiconductor film whose surfaces are modified by an organic material or an inorganic material as a result of carrying out Steps A through D (D1, D2).

Then, it is possible to prepare a sensor by connecting electrodes to the porous oxide semiconductor film.

For example, when the electrodes and the porous oxide semiconductor film are to be connected to each other in an arrangement as shown in FIG. 2, the porous material and the electrodes can be connected well to each other by firstly forming the electrodes on a substrate and subsequently carrying put the Steps A through D.

In the case of an arrangement as shown in FIG. 7, a porous oxide semiconductor film is formed on a substrate first and then electrodes are formed thereon.

In the case of an arrangement as shown in FIG. 8, electrodes are formed on the substrate first and then a porous oxide semiconductor film is formed thereon. Alternatively, a porous oxide semiconductor film is formed on a substrate made of an electrode material and then an electrode is formed on the porous oxide semiconductor film.

The process of forming electrodes may be conducted before or/and after Steps A through D for forming a porous oxide semiconductor film.

When an oxide material is used, preferably it is a material that does not give rise to any chemical change due to an etching operation that may be conducted in the course of forming a porous oxide semiconductor film. More specifically, the use of gold (Au) or platinum (Pt) is preferable.

However, any electrode material may be used for the purpose of the present invention if it does not give rise to any change in terms of profile and physical, chemical and/or electric properties thereof in the course of forming a porous oxide semiconductor film.

Techniques that can be used for forming electrodes for the purpose of the present invention include vacuum evaporation, sputtering, electro-deposition and other popular metal electrode forming methods.

EXAMPLES

Example 1

An Example where the Pore Surfaces are Coated with an Organic Material: an Organic Material Containing Aminopropyl Groups In this example, a gas sensor element was prepared by forming a tin oxide porous thin film on a substrate that carries comb-shaped electrodes formed thereon for the purpose of selectively detecting carbon monoxide (CO).

Firstly, comb-shaped electrodes of platinum (Pt) were formed on a quartz substrate by photolithography in such a way that they were separated from each other by a distance of 20 μm and have a length of 370 mm.

Then, 2.9 g of tin (II) chloride anhydride was added to 10 g of ethanol, which was then agitated for 30 minutes. Then, 1.0 g of tri-block copolymer P123 <HO(CH$_2$CH$_2$O)$_{20}$(CH$_2$CH(CH$_3$)O)$_{70}$(CH$_2$CH$_2$O)$_{20}$H> was dissolved in the ethanol, which was then agitated for another 30 minutes to produce a precursor solution A.

Thereafter, the precursor solution A was applied to the comb-shaped electrodes of the substrate by dip-coating.

Then, the substrate to which the precursor solution A was applied was moved into an environmental testing equipment and held in it.

The temperature and the relative humidity in the environmental testing equipment were controlled in a manner as described below.

The inside was held to 40° C. and 20% RH for 10 hours→The temperature and the relative humidity were caused to change over 1 hour→The inside was held to 50° C. and 90% RH for 5 hours→The temperature and the relative humidity were caused to change over 1 hour→The inside was brought back to 40° C. and 20% RH.

As a result of the above-described steps, a thin film of a surfactant-tin oxide meso structure was obtained.

Thereafter, the substrate was taken out from the environmental testing equipment and put into a muffle furnace and the temperature was raised to 300° C. in air at a rate of 1° C./min and held to that temperature for 5 hours to remove the surfactant and obtain a mesoporous tin oxide thin film.

After the removal of the surfactant, it was confirmed by infrared spectrophotometry and the like that no organic material attributable to the surfactant existed on the thin film.

When the surface and cross section of the thin film were observed through an SEM, tube-shaped structures were observed on the surface.

The cross section showed fine pores arranged like a honeycomb.

As a result of X-ray diffraction analysis, a clear diffraction peak that corresponds to an interplanar spacing of 4.9 nm was observed and a diffraction pattern that suggests a two-dimensional hexagonal structure was obtained.

However, as a result of the observation of the cross section through an SEM, it was found that the hexagonal structure was shrunk in the direction of the height of the film and hence it was not an ideal hexagonal structure.

As a result of measuring the extent of nitrogen gas adsorption, it was found that the sizes of the fine pores showed a simple dispersion with a maximum value of 5.2 nm and that the distribution curve was found within a range not smaller than 1 nm and not greater than 10 nm.

The specific surface area was about 170 m$^2$/g.

Thus, it was confirmed that the thin film was a porous thin film that had substantially uniform mesopores and a large specific surface area.

As a result of an X-ray diffractmetric analysis using obliquely incident X-rays, a clear peak ascribable to Cassiterite was confirmed.

The average crystal size L was determined to be equal to 2.7 nm by using the Scheller's formula shown below from the half breadth B (rad) and the peak position 2θ of the peak attributable to the (211) plane in the region of 2θ=45°-58° out of the appeared peaks.

$$L = 0.9\lambda/B \cos\theta$$

From the above-described facts, it was confirmed that it is possible to form a porous tin oxide thin film having a pore structure of meso region that shows regularity and microcrystals in the pore walls on an electrode substrate.

Then, the prepared porous tin oxide thin film was immersed in 10 g of ethanol solution with 0.5 g of 3-aminopropyltrimethoxysilane, which is a silane coupling agent.

Thereafter, the porous tin oxide thin film was washed in a flow of pure water and finally subjected to a dry process at 100° C. for 5 hours to modify the surfaces of the fine pores by means of an organic material containing aminopropyl groups.

In order to confirm the modification of the surfaces of the fine pores by the organic material, another porous tin oxide thin film was prepared on a high resistance silicon substrate by way of the above-described steps and the surfaces of the fine pores thereof were modified by an organic material containing aminopropyl groups. Then, the thin film was subjected to a measurement of infrared absorption spectrum.

As a result, the presence of an absorption spectrum attributable to amino groups was confirmed in the vicinity of 3,310-3,500 cm$^{-1}$.

For the purpose of comparison, a tin oxide thin film prepared without using a surfactant and hence having no mesopores was subjected to a modification process and the obtained thin film was subjected to a measurement of FT-IR absorption spectrum.

As a result of comparing the spectrums of the two specimens, the one having mesopores was confirmed to show a much stronger absorption effect. Thus, it was confirmed that the tin oxide thin film having mesopores was modified to a larger extent.

Then, 7.7 mg of 3,4-dihydroxybenzoic acid was dissolved into 10 g of water, to which 9.3 mg of carbodiimide was added and the aqueous solution was agitated.

Thereafter, the tin oxide thin film having mesopores, whose surfaces were treated by the silane coupling agent, was immersed in the solution for 24 hours.

Subsequently, the tin oxide thin film was washed in a flow of pure water and finally dried at 100° C. for 1 hour.

In order to confirm the modification by the organic material, the treated sample was subjected to a measurement of infrared absorption spectrum to find that an absorption spectrum attributable to hydroxy groups appeared in the vicinity of 3,450 cm$^{-1}$.

Such an absorption spectrum was not observed from the tin oxide thin film that was only treated by a silane coupling agent. Thus, it was confirmed that the 3,4-dihydroxybenzoic acid having hydroxy groups reacted with the silane coupling agent and the reaction product was formed on the surfaces of the fine pores.

Figure 11:
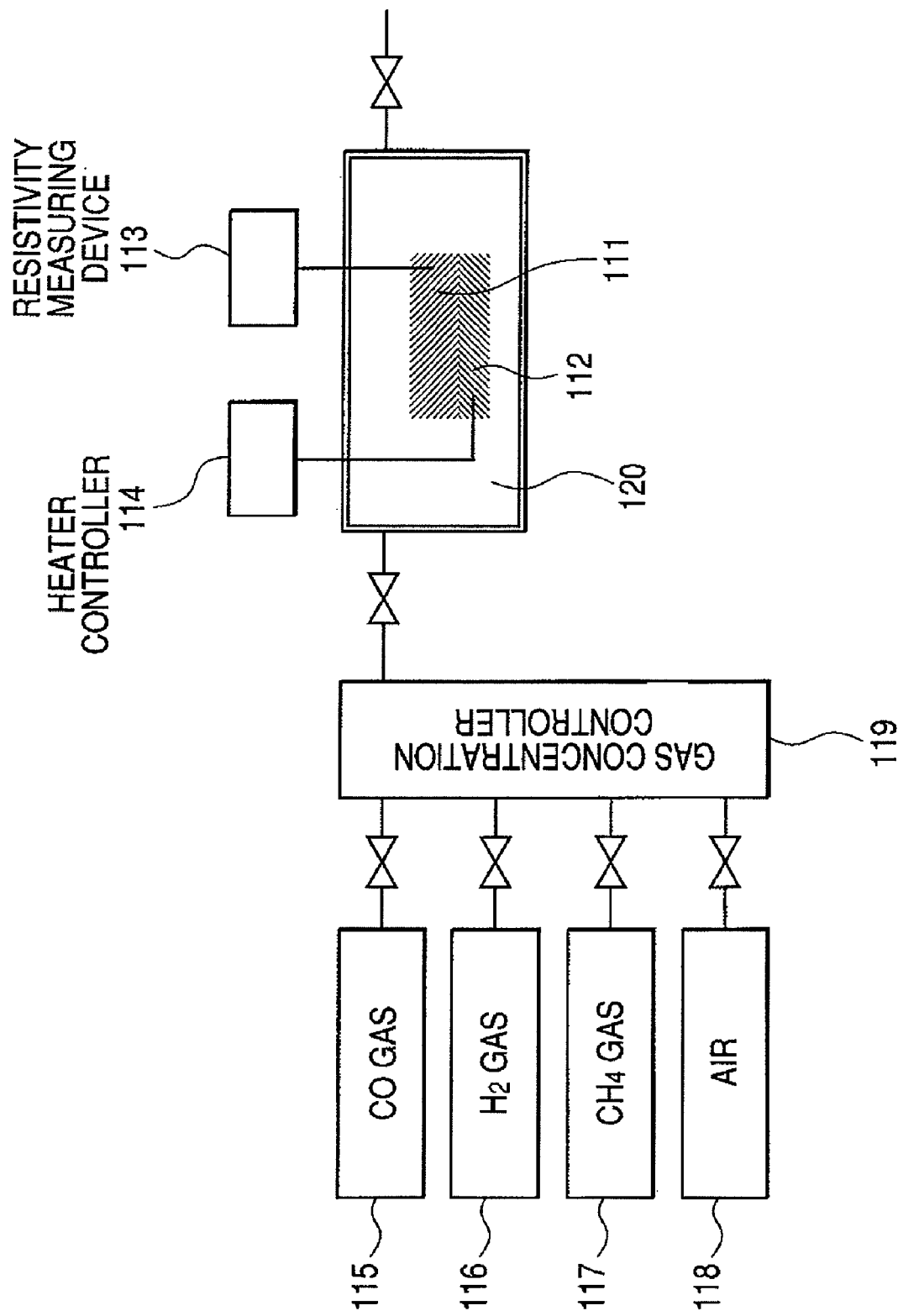
FIG. 11 is a schematic illustration of an apparatus for evaluating the characteristics of a sensor according to the invention.

Then, a gas sensor was prepared by connecting the electrode substrate on which the tin oxide porous thin film was formed to an electric circuit and the sensor characteristics of the gas sensor relative to mixed gas were measured by means of a measuring apparatus as illustrated in FIG. 11.

Three different types of mixed gas were used for the measurement. They include a mixed gas of air and carbon monoxide (CO), a mixed gas of air and methane ($CH_4$) and a mixed gas of air and hydrogen ($H_2$).

The concentration of each mixed gas could be adjusted by changing the mixing ratio of air and the gas to be detected. In this example, the concentration of each mixed gas was adjusted to 1,000 ppm and 500 ppm for measurement. The measurement was conducted in a flow system under the atmospheric pressure.

The method used for the measurements will be described below.

Only air was allowed to flow for 10 minutes→mixed gas with concentration of 1,000 ppm was allowed to flow for 20 minutes→only air was allowed to flow for 20 minutes→mixed gas with concentration of 500 ppm was allowed to flow for 20 minutes→only air was allowed to flow.

A DC current of 1V was applied between the electrodes of the sensor element to observe the electric current, while flowing air and mixed gas in the above-described order, and the observed electric current was reduced to resistivity.

The temperature of the element was held to 100° C. during the measurement.

Figure 12:
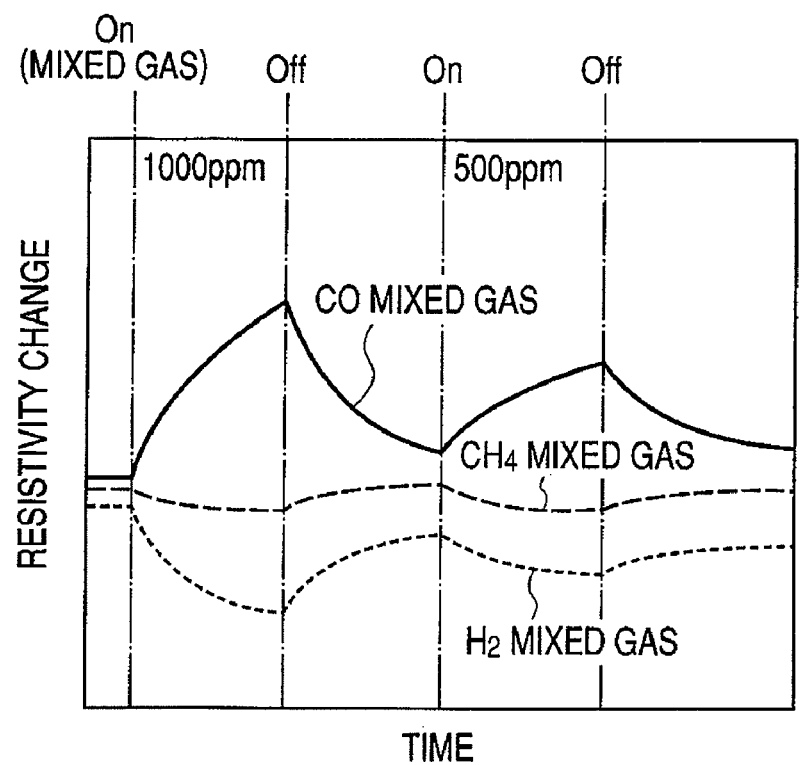
FIG. 12 is a graph illustrating the changes in the electric resistance observed when a plurality of gases is detected by means of a sensor according to the invention.

FIG. 12 is a graph illustrating the change with time of the resistivity relative to each of the mixed gases when measured under the above-described conditions.

From FIG. 12, it was confirmed that the gas sensor element comprising a tin oxide porous thin film, the surfaces of the fine pores of which were modified by an organic material, of this example showed a raised resistivity only to the mixed gas of CO and air so that it selectively detect CO.

If the resistivity of the gas sensor before the introduction of the CO mixed gas is Ra, the smallest value of the resistivity after the introduction of the CO mixed gas is Rco and the sensitivity Sco of the gas sensor element is expressed by the formula below, S=6 when the CO mixed gas of a concentration of 1,000 ppm was allowed to flow and S=2.5 when the CO mixed gas of a concentration of 500 ppm was allowed to flow.

$Sco=Rco/Ra$

From the above-described results, it was confirmed in this example that it is possible to prepare a metal oxide semiconductor type gas sensor element that shows selectivity relative to a specific gas and can highly sensitively detect the specific gas by using a tin oxide porous thin film, the surfaces of the fine pores of which are modified by an organic material.

Comparative Example 1

Figure 13:
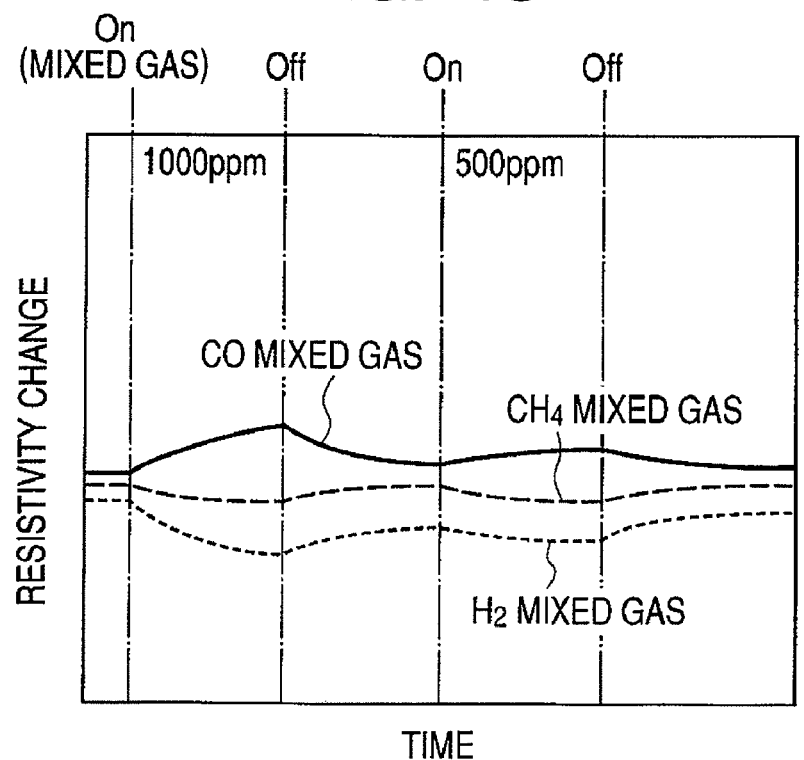
FIG. 13 is a graph illustrating the changes in the electric resistance observed when a plurality of gases is detected by means of a sensor prepared for the purpose of comparison with a sensor according to the invention.

FIG. 13 shows some of the results obtained by conducting a similar measurement on a gas sensor prepared by means of the method described in Example 1 except that tri-block copolymer P123 was not added.

The prepared gas sensor element selectively reacted to CO and air but the changing rate of the electric resistivity was low if compared with the gas sensor element prepared and used for the measurement in Example 1. More specifically, the sensitivity of the gas sensor element was S=1.1 for the CO mixed gas of a concentration of 1,000 ppm and S=1.05 for the CO mixed gas of a concentration of 500 ppm.

The changing rate of the electric resistivity was also low when $H_2$ mixed gas or $CH_4$ mixed gas was introduced if compared with the gas sensor element of Example 1.

Example 2

An Example where the Pore Surfaces are Coated with an Organic Material: an Organic Material Containing Aminopropyl Groups In this example, a mesoporous tin oxide thin film was prepared as in Example 1 except that 0.7 g of tri-block copolymer F127 <$HO(CH_2CH_2O)_{106}(CH_2CH(CH_3)O)_{70}(CH_2CHO)_{106}OH$> was used instead of 1.0 g of tri-block copolymer P123 <$HO(CH_2CH_2O)_{20}(CH_2CH(CH_3)O)_{70}(CH_2CH_2O)_{20}H$> when preparing the precursor solution.

When the surface and cross section of the thin film were observed through an SEM, the surface showed a structure where fine pores are arranged regularly and the fine pores were shrunk in the direction of the height of the film.

The cross section also showed fine pores arranged regularly.

As a result of X-ray diffraction analysis, a clear diffraction peak that corresponds to an interplanar spacing of 6.2 nm was observed.

Thus, it is safe to say that the tin oxide porous thin film is a cubic structure having a large number of openings on the surface and shows regularity.

As a result of measuring the extent of nitrogen gas adsorption, it was found that the sizes of the fine pores showed a simple dispersion with a maximum value of 6.5 nm and that the distribution curve was found within a range not smaller than 2 nm and not greater than 12 nm.

The specific surface area was about 200 $m^2/g$.

Thus, it was confirmed that the thin film was a porous thin film that had substantially uniform mesoppres and a large specific surface area.

The average crystal size L was determined to be equal to 2.7 nm by using the Scheller's formula as in Example 1.

From the above-described facts, it was confirmed that it is possible to form a porous tin oxide thin film having a pore structure of the meso region that shows regularity and microcrystals in the pore walls on an electrode substrate.

Then, the surfaces of the fine pores of the mesoporous tin oxide thin film were modified by an organic material as in Example 1 and the sensor characteristics of the gas sensor of this example relative to mixed gases were measured by using the same apparatus and method as those of Example 1. Then, it was found that the changing rate with time of the electric resistivity relative to each of the mixed gases was substantially same as its counterpart of Example as shown in FIG. 12.

From the above-described results, it was confirmed in this example that it is possible to prepare a metal oxide semiconductor type gas sensor element that shows selectivity relative to a specific gas and can highly sensitively detect the specific gas by using a tin oxide porous thin film, the surfaces of the fine pores of which are modified by an organic material.

Example 3

An Example where the Pore Surfaces are Coated with an Inorganic Material: Silicon Oxide In this example, a gas sensor element was prepared by forming a tin oxide porous thin film on a substrate on which a pair of comb-shaped electrodes had been formed and used for selectively detecting $H_2$ gas.

Firstly a mesoporous tin oxide thin film was formed on a substrate, on which a pair of comb-shaped Pt electrodes had been formed, by means of a method similar to the one used in Example 2. It was confirmed that a porous tin oxide thin film having a pore structure of the meso region that shows regularity and microcrystals in the pore walls on an electrode substrate was formed as in Example 1.

Then, the prepared porous tin oxide thin film was immersed in a toluene solution showing a diethoxydimethylsilane (DEMS) concentration of 1 wt % for about 10 minutes.

Subsequently, the porous tin oxide thin film subjected to the above process was washed in a flow of pure water and finally subjected to a dry process at 100° C. for 5 hours to modify the surfaces of the fine pores by means of an organic material containing silicon.

Thereafter, the porous tin oxide thin film was baked at 300° C. for 5 hours.

In order to confirm the modification of the surfaces of the fine pores by silicon oxide, another porous tin oxide thin film was prepared on a high resistance silicon substrate by way of the above-described steps and the prepared porous tin oxide thin film was observed by means of a TEM.

For the purpose of comparison, a specimen that had not been immersed in the DEMS solution was also observed by means of a TEM.

As a result, it was confirmed that the both specimens had fine pores that were arranged regularly, they were different from each other in terms of the contrast in the surface areas of the fine pores and that, as a result of the observation by means of TEM-DES, the presence of Si on and near the surfaces of the fine pores was confirmed on the specimen that had been subjected to a DEMS immersion process.

The adsorption isotherm of each of the samples was determined and the distribution of fine pore sizes was computationally determined by the Berret-Joyner-Halenda (BJH) method to confirm that the fine pore size distribution of the specimen that had been subjected to a DEMS immersion process was found in smaller fine pore sizes.

From the above findings, it was confirmed that silicon oxide was formed in the fine pores of the porous tin oxide thin film, while the porous tin oxide thin film was maintaining the fine pore structure.

Subsequently, the sensor characteristics of the gas sensor of this example relative to mixed gases were measured by using the same apparatus and method as those of Example 1.

Figure 14:
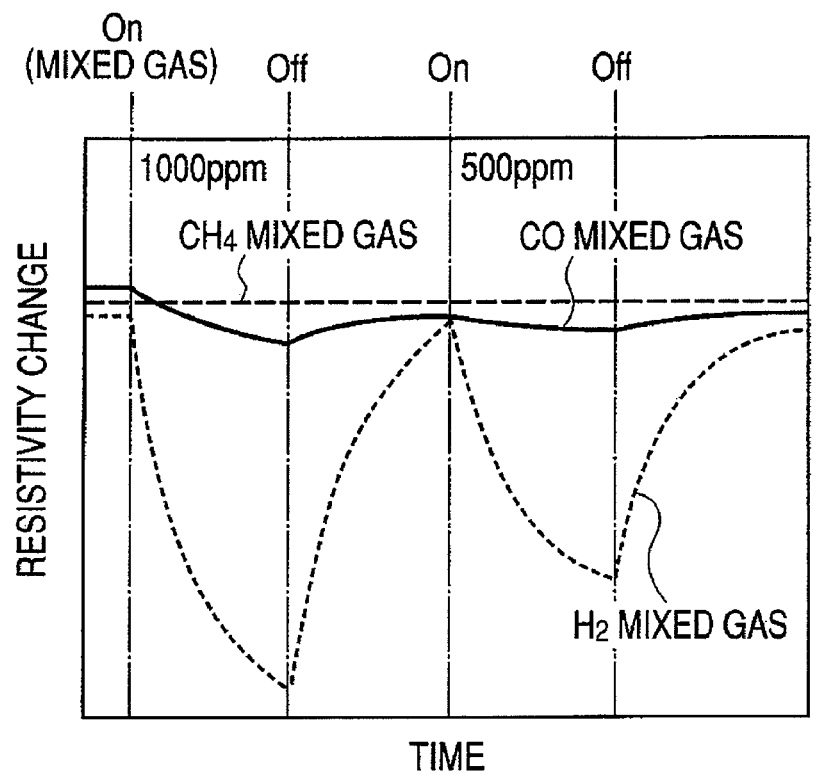
FIG. 14 is a graph illustrating the changes in the electric resistance observed when a plurality of gases are detected by means of a sensor according to the invention.

The temperature of the element was held to 150° C. during the measurement. FIG. 14 illustrates some of the obtained results.

The sensor was highly responsive relative to $H_2$ mixed gas if compared with its responsiveness relative to any other mixed gas. If the resistivity of the gas sensor before the introduction of $H_2$ mixed gas is Ra, the smallest value of the resistivity after the introduction of $H_2$ mixed gas is $RH_2$ and the sensitivity $SH_2$ of the gas sensor element is expressed by the formula below, S=300 when the $H_2$ mixed gas of a concentration of 1,000 ppm was allowed to flow and S=160 when the $H_2$ mixed gas of a concentration of 500 ppm was allowed to flow.

$$SH_2 = Ra/RH_2$$

The sensitivity of the gas sensor relative to each of the remaining mixed gases was computationally determined by using a similar formula, it was found that Sco=40 when the CO mixed gas of a concentration of 1,000 ppm was allowed to flow and $SCH_4$=3 when the $Cl_4$ mixed gas of a concentration of 1,000 ppm was allowed to flow.

From the above-described results, it was confirmed in this example that it is possible to prepare a metal oxide semiconductor type gas sensor element that shows selectivity relative to a specific $H_2$ gas and can highly sensitively detect the specific gas by using a tin oxide porous thin film that contains micro-crystals in the pore walls, and the surfaces of the fine pores of which are modified by an organic material.

Comparative. Example 2

Figure 15:
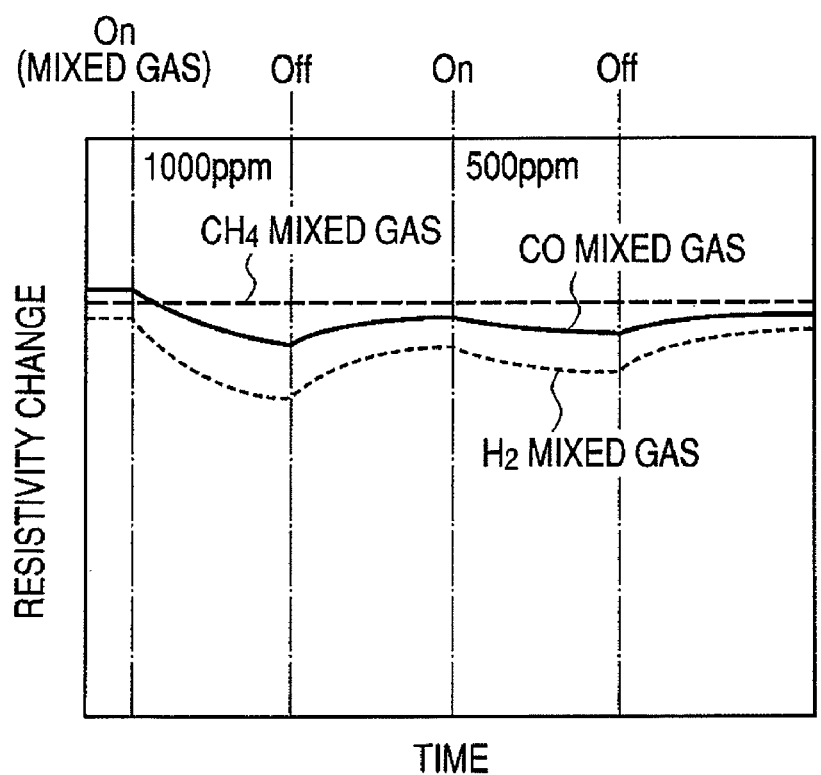
FIG. 15 is a graph illustrating the changes in the electric resistance observed when a plurality of gases are detected by means of a sensor element prepared for the purpose of comparison with a sensor according to the invention.

FIG. 15 shows some of the results obtained by conducting a similar measurement on a gas sensor prepared by means of the method described in Example 3 except that tri-block copolymer F127 was not added.

For instance, $SH_2$=30 for the $H_2$ mixed gas of a concentration of 1,000 ppm and Sco=20 for the CO mixed gas of a concentration of 1,000 ppm, whereas $SCH_4$ 1.5 for the $CH_4$ mixed gas of a concentration of 1,000 ppm. Thus, the sensitivity to any of the mixed gases was low if compared with the gas sensor element prepared in Example 3. The sensitivity was particularly low relative to $H_2$ mixed gas.

Example 4

An Example where Particles of an Inorganic Material were Held in the Pores: Metal Palladium In this example, a gas sensor element was prepared by forming a tin oxide porous thin film on a substrate on which a pair of comb-shaped electrodes had been formed and used for selectively detecting hydrogen ($H_2$) gas.

Firstly, comb-shaped electrodes of platinum (Pt) were formed on a quartz substrate by photolithography in such a way that they were separated from each other by a distance of 20 μm and have a length of 370 mm.

Then, 2.9 g of tin (II) chloride anhydride was added to 10 g of ethanol, which was then agitated for 30 minutes. Then, 1.0 g of tri-block copolymer P123 <$HO(CH_2CH_2O)_{20}(CH_2CH(CH_3)O)_{70}(CH_2CH_2O)_{20}H$> was dissolved in the ethanol, which was then agitated for another 30 minutes to produce a precursor solution A.

Thereafter, the precursor solution A was applied to the comb-shaped electrodes of the substrate by dip-coating.

Then, the substrate to which the precursor solution A was applied was moved into an environmental testing equipment and held in it. The temperature and the relative humidity in the environmental testing equipment were controlled in a manner as described below.

The inside was firstly held to 40° C. and 20% RH for 10 hours. Thereafter, the temperature and the relative humidity were caused to change over 1 hour to 50° C. and 90% RH and then held constant for 5 hours. Subsequently, the temperature and the relative humidity were brought back respectively to 40° C. and 20% RH to obtain a surfactant-tin oxide meso structure material.

Thereafter, the substrate was taken out from the environmental testing equipment and put into a muffle furnace and the temperature was raised to 300° C. in air at a rate of 1° C./min and held to that temperature for 5 hours to obtain a mesoporous tin oxide thin film.

When the surface and cross section of the film were observed through a scanning electron microscope (SEM), tube-shaped structures were observed on the surface.

The cross section showed fine pores arranged like a honeycomb.

As a result of X-ray diffraction analysis, a clear diffraction peak that corresponds to an interplanar spacing of 4.9 nm was observed and a diffraction pattern that suggests a two-dimensional hexagonal structure was obtained.

However, as a result of the observation Of the cross section through an SEM, it was found that the hexagonal structure was shrunk in the direction of the height of the film and hence it was not an ideal hexagonal structure.

As a result of measuring the extent of nitrogen gas adsorption, it was found that the sizes of the fine pores showed a simple dispersion with a maximum value of 5.2 nm and that the distribution curve was found within a range not smaller than 1 nm and not greater than 10 nm.

The specific surface area was about 170 m$^2$/g.

Thus, it was confirmed that the film was a porous film that had substantially uniform mesopores and a large specific surface area.

As a result of an X-ray diffractmetric analysis using obliquely incident X-rays to the film, a clear peak ascribable to Cassiterite was confirmed.

The average crystal size L was determined to be equal to 2.7 nm by using the Scheller's formula shown below from the half breadth B (rad) and the peak position 2θ of the peak attributable to the (211) plane in the region of 2θ=45°-58° out of the appeared peaks.

$$L=0.9\lambda/B \cos\theta$$

From the above-described facts, it was confirmed that it is possible to form a porous tin oxide thin film having a pore structure of the meso region that shows regularity and microcrystals in the pore walls on an electrode substrate.

Then, the prepared porous tin oxide thin film was immersed in an aqueous solution of ammonium where the concentration of palladium acetate (Pd(CH$_3$COO)$_2$) was 0.005M.

Subsequently, after a drying process, the solution was heated at 300° C. for 1 hour in a hydrogen atmosphere and then at 300° C. for 5 hours in the air and subjected to a reduction process again at 300° C. in a hydrogen atmosphere in order to obtain metal palladium particles.

In order to confirm that metal palladium particles were held in the pores, the structure of the surface and that of the cross section of the thin film were observed through a transmission electron microscope (TEM)

As a result, it was confirmed that particles of a diameter of about 3 nm were held in the pores. When the particles were analyzed by means of an energy dispersion type X-ray spectrometer (EDS) and an electron energy loss spectrometer (EELS) annexed to the TEM to confirm that the particles held in the pores were those of metal palladium.

As a result of X-ray diffraction analysis, a diffraction pattern that suggests a two-dimensional hexagonal structure was obtained. Thus, it was confirmed that the pore structure was maintained after causing palladium particles to be held in the pores.

As a result of measuring the extent of nitrogen gas adsorption, it was found that the specific surface area was about 180 m$^2$/g and hence had not changed significantly after causing palladium particles to be held in the pores.

Then, the electrode substrate where the tin oxide porous film was formed was connected to an electric circuit and the sensor characteristics of the gas sensor of this example relative to mixed gas were measured by means of a measuring apparatus as illustrated in FIG. 11.

Three different types of mixed gases were used for the measurement. They include a mixed gas of air and hydrogen (H$_2$) (to be referred to as gas A hereinafter), a mixed gas of air and methane (CH$_4$) (to be referred to as gas B hereinafter) and a mixed gas of air and nitrogen monoxide (NO) (to be referred to as gas C hereinafter).

The concentration of each mixed gas could be adjusted by changing the mixing ratio of air and the gas to be detected. In this example, the concentration of each mixed gas was adjusted to 200 ppm, 100 ppm and 50 ppm to measure the change in the resistivity relative to the gas concentrations.

The measurement was conducted in a flow system under the atmospheric pressure. Each of the gases was introduced with each of the above-cited concentrations during a gas On period and only air was introduced during a gas Oft period.

A DC current of 1V was applied between the electrodes of the sensor to observe the electric current, while flowing each of the above cited mixed gases, and the change with time of the electric current was observed. The temperature of the sensor was held to 100° C. during the measurement.

Figure 16:
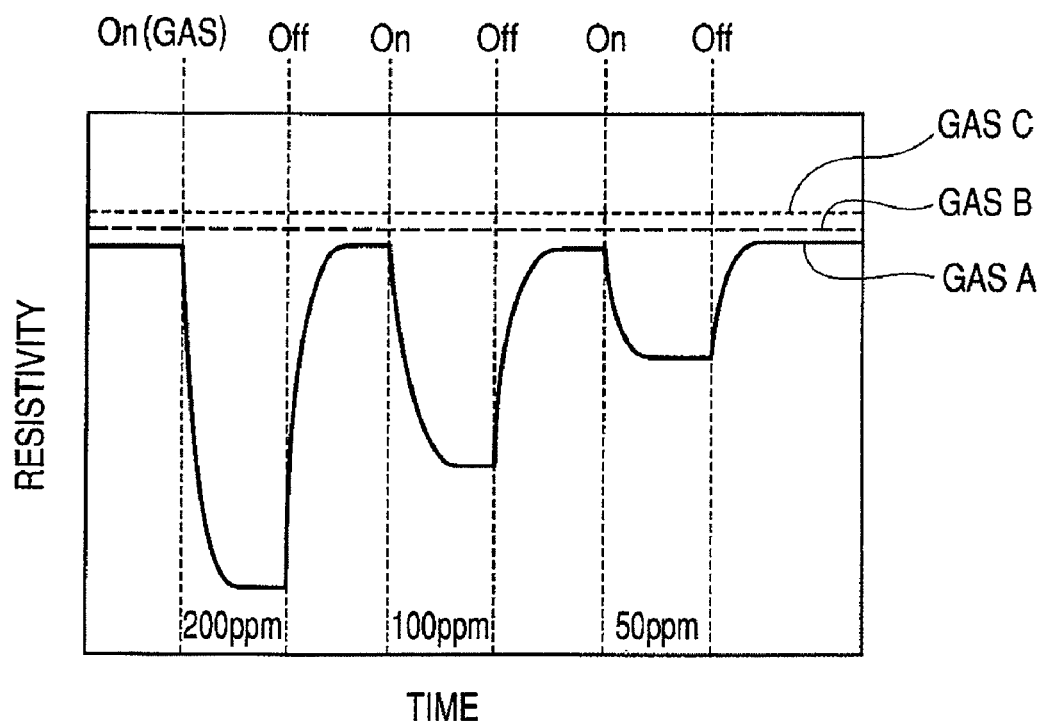
FIG. 16 is a graph illustrating the changes with time in the electric resistance observed when a plurality of gases are detected by means of a sensor according to the invention.

FIG. 16 is a graph illustrating the change with time of the resistivity relative to each of the mixed gases as determined from the change with time of the electric current.

It was found that the gas sensor of this example comprising a tin oxide porous film selectively responded to gas A, or mixed gas of air and hydrogen. In other words, it scarcely responded to gas B and gas C.

As for the change with time of the resistivity relative to gas A, if the resistivity observed in a gas Off period when only air was allowed to flow is Ra, the resistivity observed in a gas On; period when the mixed gas of air and hydrogen gas was allowed to flow is RH and the sensitivity SE of the gas sensor is defined by the formula below, it was found that SH=100 relative to hydrogen with the concentration of 200 ppm, SH=40 relative to hydrogen with the concentration of 100 ppm and SH=20 relative to hydrogen with the concentration of 50 ppm.

$$SH=Ra/RH$$

From the above-described results, it was confirmed in this example that it is possible to prepare a metal oxide semiconductor type gas sensor that shows selectivity relative to a specific gas and can highly sensitively detect the specific gas by using a tin oxide porous thin film that contains microcrystals on the pore walls and holds metal palladium particles in the pores.

Comparative Example 3

Figure 17:
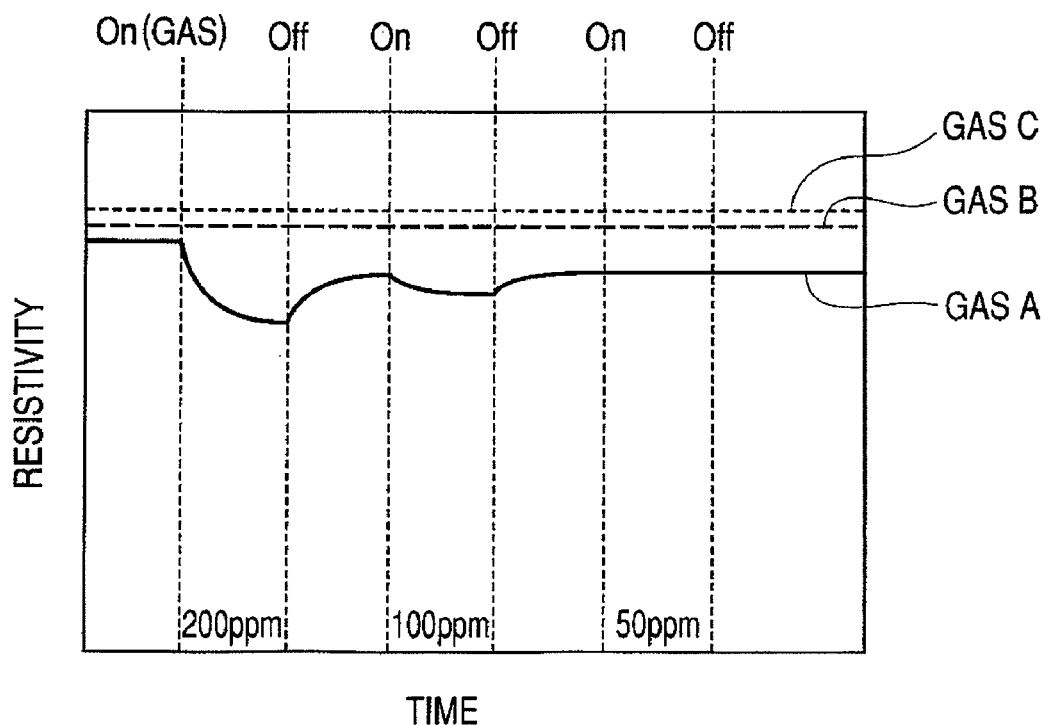
FIG. 17 is a graph illustrating the changes with time in the electric resistance observed when a plurality of gases are detected by means of a known sensor for the purpose of comparison.

FIG. 17 shows some of the results obtained by conducting a similar measurement on a gas sensor prepared by means of the method described in Example 4 except that no surfactant was added.

It reacted slightly to gas A but scarcely to gas B and gas C.

As for gas A, it was found that SH=10 relative to hydrogen with the concentration of 200 ppm, SH=4 relative to hydrogen with the concentration of 100 ppm and SH=1.5 relative to hydrogen with the concentration of 50 ppm.

Example 5

An Example where Particles of an Inorganic Material were Held in the Pores Platinum In this example, a gas sensor element was prepared by forming a tin oxide porous thin film on a substrate on which a pair of comb-shaped electrodes had been formed and used for selectively detecting H$_2$ gas.

Electrodes and a porous ton oxide film were prepared on a quartz substrate as in Example 4.

Then, the prepared porous tin oxide film was immersed in an aqueous solution of platinic chloride ($H_2PtCl_6$), where the concentration of platinic chloride was 0.005M.

Thereafter, the porous tin oxide film was subjected to a drying process and then to a reduction process at 170° C. for 2 hours in a hydrogen atmosphere in order to obtain platinum particles.

In order to confirm that platinum particles were held in the pores, the structure of the surface and that of a cross section of the thin film were observed through a transmission electron microscope (TEM).

As a result, it was confirmed that particles of a diameter of about 3 nm were held in the pores.

When the particles were analyzed by means of an energy dispersion type X-ray spectrometer (EDS) and an electron energy loss spectrometer (EELS) annexed to the TEM to confirm that the particles held in the pores were those of metal platinum.

As a result of X-ray diffraction analysis, a diffraction pattern that suggests a two-dimensional hexagonal structure was obtained. Thus, it was confirmed that the pore structure was maintained after causing platinum particles to be held in the pores.

As a result of measuring the extent of nitrogen gas adsorption, it was found that the specific surface area was about 180 $m_2/g$ and hence had not changed significantly after causing palladium particles to be held in the pores.

The sensor characteristics of the gas sensor of this example relative to mixed gases were observed by means of an apparatus and a method similar to those of Example 4 to find that the change with time of the resistivity to each of the gases of the gas sensor of this example was similar to the one illustrated in FIG. 16.

For the purpose of comparison, a similar gas sensor was prepared except that no surfactant was added and subjected to a similar observation to find that the change with time of the resistivity of this gas sensor was similar to the one illustrated in FIG. 17.

From the above-described results, it was confirmed in this example that it is possible to prepare a metal oxide semiconductor type gas sensor element that shows selectivity relative to a specific gas and can highly sensitively detect the specific gas by using a tin oxide porous film that contains microcrystals on the pore walls and holds platinum particles in the pores.

Example 6

An Example where Particles of an Inorganic Material were Held in the Pores: Copper (II) Oxide In this example, a gas sensor element was prepared by forming a tin oxide porous film on a substrate on which a pair of comb-shaped electrodes had been formed and used for selectively detecting hydrogen sulfide ($H_2S$) gas.

Electrodes and a porous tin oxide film were prepared as in Example 4.

Then, the prepared porous tin oxide film was immersed in an aqueous solution in which copper (Cu) particles prepared by laser abrasion were dispersed and subjected to a supersonic process for about 1 hour. Then, it was heated at 300° C. for 1 hour in the air so as to introduce particles of copper (II) oxide (CuO) into the pores.

In order to confirm, that particles of copper (II) oxide (CuO) were held in the pores, the structure of the surface and that of the cross section of the thin film were observed through a transmission electron microscope (TEM).

As a result, it was confirmed that particles of a diameter of about 3 nm were held in the pores.

When the particles were analyzed by means of an energy dispersion type X-ray spectrometer (EDS) and an electron energy loss spectrometer (EELS) annexed to the TEM to confirm that the particles held in the pores were those of copper (II) oxide.

As a result of X-ray diffraction analysis, a diffraction pattern that suggests a two-dimensional hexagonal structure was obtained. Thus, it was confirmed that the pore structure was maintained after causing particles of copper (II) oxide to be held in the pores.

As a result of measuring the extent of nitrogen gas adsorption, it was found that the specific surface area was about 180 $m_2/g$ and hence had not changed significantly after causing copper (II) oxide particles to be held in the pores.

The sensor characteristics of the gas sensor of this example relative to mixed gases were observed by means of an apparatus and a method similar to those of Example 4, But, mixed gas of air and hydrogen sulfide (H2S) was applied as gas A instead of mixed gas of air and hydrogen (H2) in this example. Consequently, the change with time of the resistivity to each of the gases of the gas sensor of this example was similar to the one illustrated in FIG. 16.

For the purpose of comparison, a similar gas sensor was prepared except that no surfactant was added and subjected to a similar observation to find that the change with time of the resistivity of this gas sensor was similar to the one illustrated in FIG. 17.

From the above-described results, it was confirmed in this example that it is possible to prepare a metal oxide semiconductor type gas sensor element that shows selectivity relative to a specific gas and can highly sensitively detect the specific gas by using a tin oxide porous thin film that contains microcrystals on the pore walls and holds particles of copper (II) oxide in the pores.

A sensor and a method of manufacturing the same according to the invention can be applied to a gas sensor for selectively detecting a particular type of gas. Additionally, a sensor according to the present invention can find applications in the field of gas sensors for detecting gas and bio sensors for detecting bio substances.

Furthermore, a sensor and a method of manufacturing the same according to the invention can find applications in the field of gas sensors for selectively detecting a particular type of gas.

This application claims priority from Japanese Patent Application Nos. 2004-329046 filed on Nov. 12, 2004, 2004-376368 filed on Dec. 27, 2004 and filed on Jun. 7, 2005, which are hereby incorporated by reference herein.

What is claimed is:

1. A method of manufacturing a sensor comprising the steps of:
   preparing a reaction solution containing a metal compound and a surfactant to apply the reaction solution onto a substrate;
   holding the substrate with the reaction solution applied thereto in a steam-containing atmosphere to form a film containing a metal oxide and the surfactant on the substrate;
   removing the surfactant from the film to produce a film having a plurality of mesopores; and
   causing the mesopores to hold particles of an inorganic material.

2. A method of manufacturing a sensor comprising the steps of:
preparing a reaction solution containing a metal compound and a surfactant to apply the reaction solution onto a substrate;
holding the substrate with the reaction solution applied thereto in a steam-containing atmosphere to form a film containing a metal oxide and the surfactant on the substrate;
removing the surfactant from the film to produce a film having a plurality of mesopores; and
coating at least part of surfaces in the mesopores with an organic material.

3. A method of manufacturing a sensor comprising the steps of:
preparing a reaction solution containing a metal compound and a surfactant to apply the reaction solution onto a substrate;
holding the substrate with the reaction solution applied thereto in a steam-containing atmosphere to form a film containing a metal oxide and the surfactant on the substrate;
removing the surfactant from the film to produce a film having a plurality of mesopores; and
coating at least part of surfaces in the mesopores with an oxide.

4. The method according to claim 1, wherein the metal compound is a chloride containing a metal, an alkoxide containing a metal or an isopropoxide containing a metal.

5. The method according to claim 1, wherein
the surfactant contains ethylene oxide as a hydrophilic group.

6. The method according to claim 1, wherein
the step of causing the mesopores to hold particles of an inorganic material includes a step of introducing an inorganic compound or an inorganic material into the mesopores and a step of forming particles of an inorganic material or an inorganic oxide in the mesopores by oxidizing or reducing the inorganic compound or the inorganic material.

7. The method according to claim 2, wherein the step of coating at least part of surfaces in the mesopores with an organic material is a step of bonding the organic material to the surfaces by means of a silane coupling agent.

* * * * *